(12) United States Patent
Djupesland et al.

(10) Patent No.: US 7,934,503 B2
(45) Date of Patent: May 3, 2011

(54) DELIVERY DEVICES

(75) Inventors: Per Gisle Djupesland, Oslo (NO);
Matthew Egerton Young,
Cambridgeshire (GB); Andrew Robert Fry, Hertfordshire (GB); Christopher John Hurlstone, Essex (GB)

(73) Assignee: Optinose AS, Oslo (NO)

( * ) Notice: Subject to any disclaimer, the term of this patent is extended or adjusted under 35 U.S.C. 154(b) by 1369 days.

(21) Appl. No.: 10/520,957

(22) PCT Filed: Jul. 9, 2003

(86) PCT No.: PCT/GB03/02961
§ 371 (c)(1),
(2), (4) Date: Nov. 30, 2005

(87) PCT Pub. No.: WO2004/004922
PCT Pub. Date: Jan. 15, 2004

(65) Prior Publication Data
US 2006/0169278 A1   Aug. 3, 2006

(30) Foreign Application Priority Data

Jul. 9, 2002  (GB) .................................. 0215904.4
Nov. 22, 2002 (GB) .................................. 0227345.6

(51) Int. Cl.
*A61M 15/08* (2006.01)
*A61M 16/00* (2006.01)
(52) U.S. Cl. ......... 128/207.18; 128/203.21; 128/205.21; 128/207.14
(58) Field of Classification Search ............. 128/203.12, 128/203.15, 203.21, 205.21, 207.14, 207.18
See application file for complete search history.

(56) References Cited

U.S. PATENT DOCUMENTS

| 1,715,986 | A |   | 6/1929 | Brown |
| 1,971,345 | A | * | 8/1934 | Hein .............................. 604/212 |
| D177,044 | S | * | 3/1956 | Hassler et al. ................ D24/115 |
| 3,822,702 | A | * | 7/1974 | Bolduc et al. ................. 128/831 |
| 3,871,374 | A | * | 3/1975 | Bolduc et al. ................. 128/831 |

(Continued)

FOREIGN PATENT DOCUMENTS

BE          483 886         7/1948

(Continued)

OTHER PUBLICATIONS

U.S. Appl. No. 12/161,466, filed Jul. 18, 2008, Djupesland.

(Continued)

*Primary Examiner* — Steven O Douglas
*Assistant Examiner* — Clinton Ostrup
(74) *Attorney, Agent, or Firm* — Kristin H. Neuman, Esq.; Isaac A. Hubner, Esq.; Proskauer Rose LLP

(57) ABSTRACT

A delivery device for and method of delivering substance, the delivery device comprising: a delivery outlet (7) from which substance (S) is in use delivered; a gas chamber (17) containing a gas and being of reducible volume, wherein a reduction in the volume of the gas chamber (17) to a predeterminable volume acts to pressurize the contained gas to a predeterminable pressure; a seal element (11) disposed between the gas chamber (17) and the delivery outlet (7); and an opening mechanism configured, on reduction of the volume of the gas chamber to a predeterminable volume, to open the seal element (11), whereupon a gas flow from the gas chamber (17) acts to deliver substance (S) from the delivery outlet (7).

41 Claims, 13 Drawing Sheets

U.S. PATENT DOCUMENTS

| | | | |
|---|---|---|---|
| 3,948,259 A * | 4/1976 | Bolduc et al. | 128/831 |
| 3,972,331 A * | 8/1976 | Bolduc et al. | 604/97.02 |
| 3,989,045 A * | 11/1976 | Van Eck | 604/203 |
| 4,282,986 A * | 8/1981 | af Ekenstam et al. | 222/1 |
| 4,457,453 A | 7/1984 | Stevens et al. | |
| 5,215,221 A | 6/1993 | Dirksing | |
| 5,328,099 A * | 7/1994 | Petit et al. | 239/372 |
| D361,380 S * | 8/1995 | Linner | D24/115 |
| 5,542,411 A * | 8/1996 | Rex | 128/203.15 |
| 5,683,361 A * | 11/1997 | Elk et al. | 604/58 |
| 6,062,213 A * | 5/2000 | Fuisz et al. | 128/200.21 |
| 6,098,619 A * | 8/2000 | Britto et al. | 128/203.15 |
| D432,647 S * | 10/2000 | Farris | D24/115 |
| 6,443,125 B1 * | 9/2002 | Mendler | 123/316 |
| 6,715,485 B1 | 4/2004 | Djupesland | |
| 6,866,039 B1 * | 3/2005 | Wright et al. | 128/203.15 |
| 7,163,013 B2 * | 1/2007 | Harrison | 128/203.21 |
| 7,347,201 B2 | 3/2008 | Djupesland | |
| 7,377,901 B2 | 5/2008 | Djupesland et al. | |
| 7,481,218 B2 | 1/2009 | Djupesland | |
| 7,543,581 B2 | 6/2009 | Djupesland | |
| 2002/0092523 A1 | 7/2002 | Connelly et al. | |
| 2004/0112378 A1 | 6/2004 | Djupesland | |
| 2004/0112379 A1 | 6/2004 | Djupesland | |
| 2004/0182388 A1 | 9/2004 | Djupesland | |
| 2005/0028812 A1 | 2/2005 | Djupesland | |
| 2005/0072430 A1 | 4/2005 | Djupesland | |
| 2005/0235992 A1 | 10/2005 | Djupesland | |
| 2006/0096589 A1 | 5/2006 | Djupesland | |
| 2006/0219240 A1 | 10/2006 | Djupesland | |
| 2006/0219241 A1 | 10/2006 | Djupesland | |
| 2006/0225732 A1 | 10/2006 | Djupesland | |
| 2006/0231094 A1 | 10/2006 | Djupesland | |
| 2007/0039614 A1 | 2/2007 | Djupesland | |
| 2007/0125371 A1 | 6/2007 | Djupesland | |
| 2007/0186927 A1 | 8/2007 | Djupesland et al. | |
| 2008/0161771 A1 | 7/2008 | Djupesland | |
| 2008/0163874 A1 | 7/2008 | Djupesland | |
| 2008/0221471 A1 | 9/2008 | Djupesland | |
| 2008/0223363 A1 | 9/2008 | Djupesland | |
| 2008/0289629 A1 | 11/2008 | Djupesland | |
| 2009/0101146 A1 | 4/2009 | Djupesland | |
| 2009/0293873 A1 | 12/2009 | Djupesland | |

FOREIGN PATENT DOCUMENTS

| | | |
|---|---|---|
| CA | 2020425 A * | 1/1991 |
| DE | 34 46 466 | 7/1986 |
| DE | 10032937 A1 * | 1/2001 |
| EP | 0 407 276 | 1/1991 |
| FR | 967 505 | 11/1950 |
| FR | 1 051 645 | 1/1954 |
| FR | 2 753 438 | 3/1998 |
| GB | 2 367 756 | 4/2002 |
| WO | 91/06333 | 5/1991 |
| WO | 93/11818 | 6/1993 |
| WO | 98/58695 | 12/1998 |
| WO | 00/21841 | 4/2000 |
| WO | 02/056950 | 7/2002 |

OTHER PUBLICATIONS

U.S. Appl. No. 12/279,285, filed Aug. 13, 2008, Djupesland.
U.S. Appl. No. 12/279,291, filed Aug. 13, 2008, Djupesland.
U.S. Appl. No. 12/281,547, filed Sep. 3, 2008, Djupesland.
U.S. Appl. No. 12/281,894, filed Sep. 5, 2008, Djupesland.
U.S. Appl. No. 12/293,972, filed Sep. 22, 2008, Djupesland.
U.S. Appl. No. 12/298,292, filed Oct. 23, 2008, Djupesland.
U.S. Appl. No. 12/303,667, filed Dec. 5, 2008, Djupesland.
U.S. Appl. No. 12/375,115, filed Jan. 26, 2009, Djupesland.
U.S. Appl. No. 12/516,399, filed May 27, 2009, Djupesland.
U.S. Appl. No. 12/516,401, filed May 27, 2009, Djupesland.
U.S. Appl. No. 12/516,404, filed May 27, 2009, Djupesland.
U.S. Appl. No. 12/594,361, filed Oct. 2, 2009, Djupesland et al.
U.S. Appl. No. 12/594,365, filed Oct. 2, 2009, Djupesland et al.

* cited by examiner

DELIVERY DEVICES

This application is a national phase of International Application No. PCT/GB2003/002961 filed Jul. 9, 2003 and published in the English language.

The present invention relates to a delivery device for and a method of delivering substance, in particular one of a liquid, as a suspension or solution, or a powder, and especially nasal and oral delivery device for delivering substances containing a medicament, especially systemic or topical pharmaceuticals, or a vaccine.

Nasal and oral delivery of powdered and liquid substances has been established for some time and there are numerous products on the market which provide for such delivery.

As regards nasal delivery, there are many nasal conditions which require treatment. One such condition is nasal inflammation, specifically rhinitis, which can be allergic or non-allergic and is often associated with infection and prevents normal nasal function. By way of example, allergic and non-allergic inflammation of the nasal airway can typically effect between 10 and 20% of the population, with nasal congestion of the erectile tissues of the nasal concha, lacrimation, secretion of watery mucus, sneezing and itching being the most common symptoms. As will be understood, nasal congestion impedes nasal breathing and promotes oral breathing, leading to snoring and sleep disturbance. Other nasal conditions include nasal polyps which arise from the paranasal sinuses, hypertrophic adenoids, secretory otitis media, sinus disease and reduced olfaction.

In the treatment of certain nasal conditions, the topical administration of medicaments is preferable, particularly where the nasal mucosa is the prime pathological pathway, such as in treating or relieving nasal congestion. Medicaments that are commonly topically delivered include decongestants, anti-histamines, cromoglycates, steroids and antibiotics. At present, among the known anti-inflammatory pharmaceuticals, topical steroids have been shown to have an effect on nasal congestion. Topical decongestants have also been suggested for use in relieving nasal congestion. The treatment of hypertrophic adenoids and chronic secretory otitis media using topical decongestants, steroids and anti-microbial agents, although somewhat controversial, has also been proposed. Further, the topical administration of pharmaceuticals has been used to treat or at least relieve symptoms of inflammation in the anterior region of the nasopharynx, the paranasal sinuses and the auditory tubes.

Medicaments can also be systemically delivered through the nasal pathway, the nasal pathway offering a good administration route for the systemic delivery of pharmaceuticals, such as hormones, for example, oxytocin and calcitonin, and analgetics, such as anti-migraine compositions, as the high blood flow and large surface area of the nasal mucosa advantageously provides for rapid systemic uptake.

Nasal delivery also provides for the administration of medicaments requiring a rapid onset of action, for example, analgetics, anti-emetics, insulin, anti-epileptics, sedatives and hypnotica, and also other pharmaceuticals, for example, cardio-vascular drugs. It is envisaged that nasal administration will provide for a fast onset of action, at a rate similar to that of injection and at a rate much faster than that of oral administration. Indeed, for the treatment of many acute conditions, nasal administration is advantageous over oral administration, since gastric stasis can further slow the onset of action following oral administration.

Nasal delivery also further provides an effective delivery route for the administration of proteins and peptides as produced by modern biotechnological techniques. For such substances, the metabolism in the intestines and the first-pass-effect in the liver represent significant obstacles for reliable and cost-efficient delivery.

Furthermore, nasal delivery also further provides for the treatment of many common neurological diseases, such as Alzheimer's, Parkinson's, psychiatric diseases and intracerebral infections, where not possible using existing techniques. The nasal delivery technique of the present invention allows for delivery to the olfactory region, which region is located in the superior region of the nasal cavities and represents the only region where it is possible to circumvent the blood-to-brain barrier (BBB) and enable communication with the cerebrospinal fluid (CSF) and the brain.

Still furthermore, and a prime focus of the present invention is the nasal delivery of vaccines. The nasal delivery device of the present invention has been developed with the particular aim of providing a delivery device for the mass treatment, in particular the mass vaccination, of subjects.

It is an aim of the present invention to provide an improved delivery device and delivery method, and, in particular, a low-cost, mass-producible delivery device which can provide for the generation of a gas flow at a predeterminable pressure on actuation, thereby providing for precise delivery of substance.

U.S. Pat. No. 5,215,221 discloses a disposable unit-dose delivery device for the delivery of a powdered medicament, which comprises a gas chamber separated from a substance chamber containing a powdered medicament by a frangible seal element. When pressure is applied to the gas chamber by squeezing, the gas pressure within the chamber rises and this pressure ruptures the seal element. The pressurized gas then suddenly exits through the substance chamber, where the powdered medicament is fluidized and entrained by the gas flow.

This prior art delivery device, whilst being of simple construction, suffers from the particular disadvantage that it is very difficult to fabricate the frangible seal element to provide for rupture reliably at a predetermined gas pressure, as required to fluidize and dispense substances accurately.

In one aspect the present invention provides a delivery device actuatable to deliver substance, comprising: a delivery outlet from which substance is in use delivered; a gas chamber containing a gas and being of reducible volume, wherein a reduction in the volume of the gas chamber to a predeterminable volume acts to pressurize the contained gas to a predeterminable pressure; a seal element disposed between the gas chamber and the delivery outlet; and an opening mechanism configured, on reduction of the volume of the gas chamber to a predeterminable volume, to open the seal element, whereupon a gas flow from the gas chamber acts to deliver substance from the delivery outlet.

Preferably, the gas chamber is defined in part by a flexible member to which an actuating force is in use applied in actuating the delivery device, with the actuating force acting to depress the flexible member such as to reduce the volume of the gas chamber and pressurize the gas contained therein.

More preferably, the flexible member comprises an outwardly-projecting member which is depressed on application of an actuating force.

Still more preferably, the flexible member comprises a dome-shaped member.

Preferably, the flexible member is configured such as to provide for deflection thereof in a controlled, predeterminable fashion in depressing the same on application of an actuating force.

More preferably, the flexible member is one or both of shaped or sized to provide for controlled deflection.

Still more preferably, the flexible member includes ribs which provide for controlled deflection.

In one embodiment the seal element comprises a rupturable element, and the opening mechanism includes a rupturing element which acts to rupture the rupturable element on depression of the flexible member to a predetermined extent.

In one embodiment the rupturing element is supported at an inner surface of the flexible member in opposed relation to the rupturable element such as to be moved in a direction of an actuating force as applied to the flexible member.

In another embodiment the opening mechanism comprises an actuating arm which supports the rupturing element, with the actuating arm being movably disposed relative to the rupturable element on engagement by the flexible member, such that, on depression of the flexible member to a predetermined extent, the actuating arm is moved such as to cause the rupturing element to rupture the rupturable element.

Preferably, the actuating arm is hingeably supported such that the rupturing element is rotated to rupture the rupturable element.

In a further embodiment the opening mechanism comprises a link assembly which supports the rupturing element, with the link assembly being movable relative to the rupturable element on engagement by the flexible member, such that, on depression of the flexible member to a predetermined extent, the link assembly is moved such as to cause the rupturing element to rupture the rupturable element.

Preferably, the link assembly comprises first, second and third hinged links, with the first link being hinged relative to the rupturable element, the second link supporting the rupturing element at one, forward end thereof and the third link coupling the respective other ends of the first and second links, whereby depression of the flexible member acts to hinge the first link relative to the rupturable element, which movement, through the coupling provided by the third link, acts to drive the second link forwardly to cause the rupturing element supported thereby to rupture the rupturable element.

In another embodiment the seal element comprises a valve element, and the opening mechanism is configured to release the valve element on depression of the flexible member to a predetermined extent.

Preferably, the delivery device further comprises: a gas supply passage operatively in fluid communication with the delivery outlet; and wherein the valve element is normally in a closed position in sealing engagement with the gas supply passage, and moved to an open position out of sealing engagement with the gas supply passage by the opening mechanism on depression of the flexible member to a predetermined extent.

In one embodiment the opening mechanism comprises a link assembly which supports the valve element, with the link assembly being movable relative to the gas supply passage on engagement by the flexible member, such that, on depression of the flexible member to a predetermined extent, the link assembly is moved such as to cause the valve element to be moved to the open position.

In one embodiment the link assembly comprises first, second and third hinged links, with the first link being hinged relative to the gas supply passage, the second link supporting the valve element at one, forward end thereof and the third link coupling the respective other ends of the first and second links, whereby depression of the flexible member acts to hinge the first link relative to the gas supply passage, which movement, through the coupling provided by the third link, acts to drive the second link to cause the valve element supported thereby to be moved to the open position.

Preferably, the link assembly is configured such that the valve element is withdrawn from the gas supply passage on depression of the flexible member to a predetermined extent.

In another embodiment the link assembly comprises first and second hinged links, with the first link being hinged relative to the gas supply passage and the second link supporting the valve element at one, forward end thereof, whereby depression of the flexible member acts to hinge the first link relative to the gas supply passage, which movement acts to drive the second link to cause the valve element supported thereby to be moved to the open position.

Preferably, the valve element is pushed from the gas supply passage on depression of the flexible member to a predetermined extent.

Preferably, the link assembly further comprises a supporting arm which acts normally to support the link assembly such that the valve element is in the closed position.

In a further embodiment the opening mechanism comprises an actuating arm which supports the valve element, with the actuating arm being movably disposed relative to the gas supply passage on engagement by the flexible member, such that, on depression of the flexible member to a predetermined extent, the actuating arm is moved such as to move the valve element to the open position.

Preferably, the actuating arm is hingeably supported such that the valve element is rotated from the closed position.

More preferably, the valve element comprises a flap.

In one embodiment the valve element is normally biased to the gas supply passage in the closed position.

In another embodiment the valve element is bonded to the gas supply passage in the closed position.

In one embodiment the delivery device further comprises: at least one substance chamber for containing substance operatively in fluid communication with the delivery outlet.

Preferably, the delivery device comprises: first and second substance chambers, each separately containing substance components which are combined for delivery.

In another embodiment substance may be stored within the gas chamber.

In one embodiment the delivery device is for insertion into a body cavity; and further comprising: an expansion mechanism for expanding the body cavity.

Preferably, the expansion mechanism provides for sealing engagement with the body cavity.

In one embodiment the expansion mechanism comprises first and second expansion arms disposed in opposed relationship to respective sides of the delivery outlet, and an actuation member which in use is actuated by a subject in actuating the delivery device and effects expansion of the expansion arms.

Preferably, the actuation member comprises an actuation body and first and second biasing arms extending forwardly of the actuation body such as to engage respective ones of the first and second expansion arms, whereby actuation of the actuation body acts to cause expansion of the first and second expansion arms.

More preferably, the first and second biasing arms comprise resilient elements which act to bias respective ones of the first and second biasing arms outwardly.

In another embodiment the expansion mechanism comprises first and second levers which are pivotally hinged relative to opposed sides of the delivery outlet, each of the levers comprising a first, expansion arm extending forwardly and laterally of the delivery outlet and a second, biasing arm extending rearwardly, whereby, on application of an actuation force to the biasing arms such as to bias the same inwardly, the expansion arms are driven outwardly to effect expansion of the same.

Preferably, the actuation member comprises an actuation body and first and second links which couple respective ones of the biasing arms to the actuation body.

In a further embodiment the expansion mechanism comprises a lever which is hinged relative to delivery outlet, the lever comprising a loading arm which is acted upon by a subject in actuating the delivery device, and an expansion arm extending forwardly to one side of the delivery outlet, whereby the expansion arm is moved outwardly relative to the delivery outlet on a subject acting upon the loading arm.

In one embodiment the delivery device is a nasal delivery device.

In another embodiment the delivery device is an oral delivery device.

In one embodiment substance is delivered as a liquid.

In another embodiment substance is delivered as a powder.

In another embodiment the present invention provides a delivery device, comprising: a gas-filled chamber of variable volume; a delivery outlet coupled to the chamber and from which substance is deliverable, carried by the gas from the chamber; a seal between the chamber and the delivery outlet; and opening means for opening the seal on reduction of the volume of the chamber to a predeterminable volume, to allow the gas pressurized by the reduction in the volume of the chamber to flow through the delivery outlet.

In a further aspect the present invention provides a method of delivering substance, comprising the steps of: reducing the volume of a gas-filled chamber to pressurize the gas contained therein; when the volume of the chamber is reduced to a predeterminable volume, providing a fluid connection between the chamber and a delivery outlet such as cause the pressurized gas to deliver substance from the delivery outlet.

The present invention advantageously provides an improved delivery device, which both provides for efficient delivery of substances, particularly in critical applications such as drug delivery where the delivered jet or cloud of liquid or powder needs to be tightly controlled, and in being of relatively low cost.

In a preferred embodiment the delivery device provides for delivery in a repeatable and reproducible manner, particularly as to the flow characteristics of the entraining gas flow, with actuation not being influenced by the rate of application of an actuating force, or ambient conditions, such as temperature or humidity, or previous storage conditions. Also, in its preferred embodiment, any manipulation of the characteristics of the seal element, for example, through cyclic loading of the gas chamber below its critical pressure limit, does not influence repeatability.

Also, it will be appreciated that, in providing for the seal element to be ruptured separately from the application of pressure, it is possible to "tune" a predetermined pressure at which the barrier seal is opened and to prevent premature or undesired failure of the seal due to misuse or abuse, including storage in adverse conditions.

In its preferred embodiment the present invention allows for manufacture using high-volume, low-cost technologies. "Form, fill and seal" packaging is one such technology, which utilizes vacuum forming and laminating technologies, typically using aluminium foil or polymer materials. Such packaging is well established for a range of product types, including products in the pharmaceutical sector, such as capsule blister packs and sachets for lyophilised drugs, and for a large range of other types of product, such as coffee sachets and adhesives. It is also known in many applications, and especially in non-pharmaceutical applications, to make "form, fill and seal" plastic products which incorporate welded-in injection-moulded components.

The present invention thus enables the manufacture of an effective, low-cost disposable delivery device, such as a drug delivery device, based on manufacturing processes that are separately already well-established.

Preferred embodiments of the present invention will now be described hereinbelow by way of example only with reference to the accompanying drawings, in which:

FIGS. 1 to 3 illustrate a delivery device in accordance with a first embodiment of the present invention.

Figure 1:
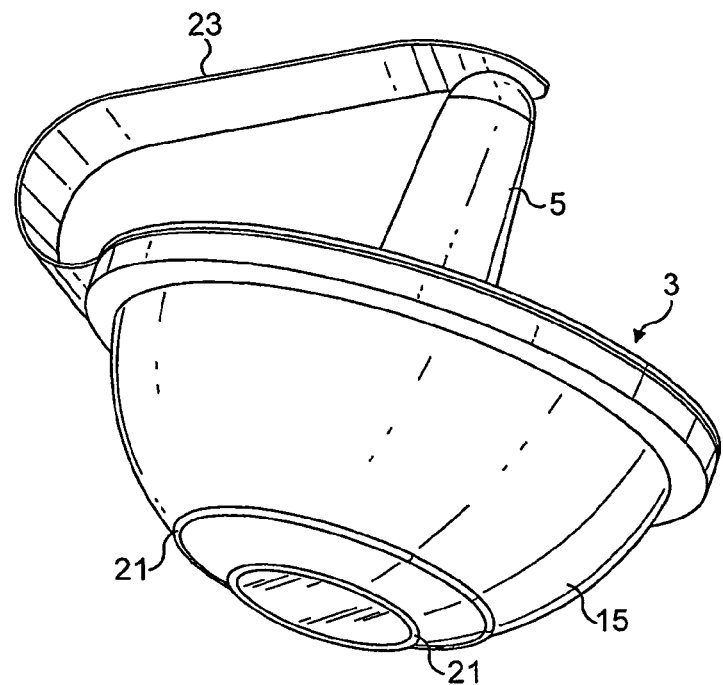
FIG. 1 illustrates a perspective view of a delivery device in accordance with a first embodiment of the present invention.
Figure 2:
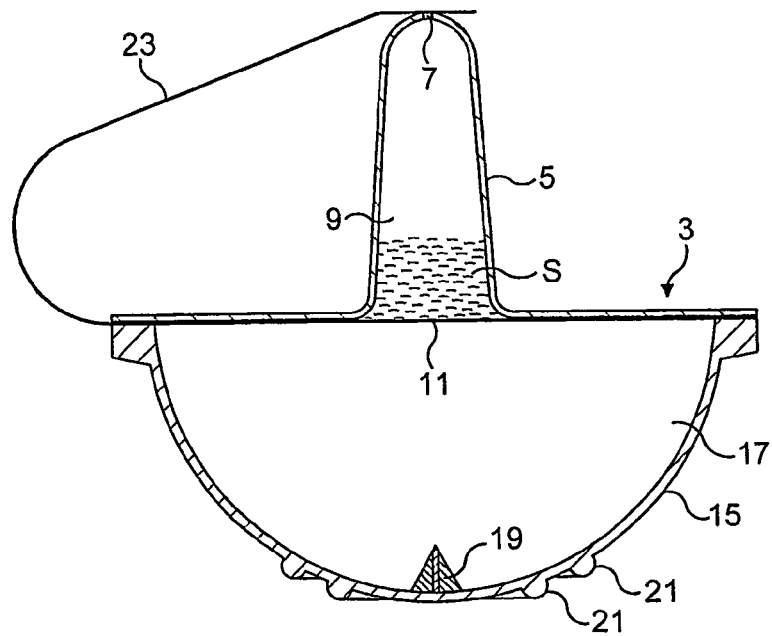
FIG. 2 illustrates a sectional view of the delivery device of FIG. 1.

In this embodiment the delivery device is configured as a unit-dose, disposable nasal delivery device for delivering substance to a nasal airway of a subject.

The delivery device comprises a body unit 3 which comprises a nosepiece 5 for insertion into a nostril of a subject which includes a delivery outlet 7 from which substance S is delivered, and a substance chamber 9 in fluid communication with the delivery outlet 7 which is defined in part by a rupturable seal element 11, in this embodiment a frangible membrane, here a film, and contains substance S to be delivered.

In this embodiment the substance S is a powder, but in another embodiment could equally be a liquid. For embodiments which deliver liquids, the delivery outlet 7 can be configured to deliver the liquid as an aerosol spray, that is, as liquid particles, or a liquid jet, that is, as a column of liquid.

In this embodiment the nosepiece 5 has an elongate tubular body, here of frusto-conical shape, which defines the substance chamber 9 and includes the delivery outlet 7 at one, forward end thereof and the seal element 11 at the other, rear end thereof.

The delivery device further comprises a flexible member 15, in this embodiment an outwardly-projecting diaphragm, here dome-shaped, typically part-spherical, and in one embodiment hemi-spherical, which is disposed to the body unit 3 such as to define a compressible gas chamber 17 which is in fluid communication with a surface of the seal element 11 which is opposite the substance chamber 9. The flexible member 15 is configured such as to be depressed by a subject in applying an actuating force F to actuate the delivery device. In depressing the flexible member 15, typically through the application of a thumb of the subject where gripping the body unit 3 in ones of the forefingers, the pressure of the gas contained in the gas chamber 17 progressively increases to generate a gas supply which is at a pressure sufficient to expel the substance S from the substance chamber 9 and through the delivery outlet 7 in the nosepiece 5.

In this embodiment the flexible member 15 supports a rupturing element 19, here a sharp spike, on the inner surface thereof which is centrally located such as to oppose the seal element 11, and, as will be described in more detail hereinbelow, acts to rupture the seal element 11 on depression of the flexible member 15 to a predetermined extent, with the actuating force F being applied in the direction of movement of the rupturing element 19. In this embodiment the seal element 11 has a rupture strength which exceeds the pressure which can be generated in the gas chamber 17, such that actuation of the delivery device requires the rupturing element 19 to rupture the seal element 11, and, in requiring the flexible member 15 to be advanced to a predetermined extent to cause the rupturing element 19 to rupture the seal element 11, the generation of a predetermined pressure in the gas chamber 17 can be ensured prior to actuation of the delivery device.

In this embodiment the flexible member 15 is configured, here including annular ribs 21, to provide for a controlled deformation of the flexible member 15 on being depressed, thereby ensuring the generation of a predetermined pressure in the gas chamber 17 at the point of the rupturing element 19 rupturing the seal element 11, and avoiding the possibility of the flexible member 15 being depressed in a non-uniform manner which could result in the rupturing element 19 reaching the seal element 11 without the predetermined gas pressure having been achieved.

In this embodiment the delivery device further comprises a closure member 23, here a sealing tape, which provides for closure of the delivery outlet 7 in the nosepiece 5 prior to use of the delivery device.

Operation of the delivery device will now be described hereinbelow.

A subject first removes the closure member 23 and inserts the nosepiece 5 into one of his/her nostrils.

The subject then depresses the flexible member 15, typically by the application of his/her thumb when gripping the body unit 3 in his/her forefingers. In depressing the flexible member 15, the rupturing element 19, as supported thereby, advances, and the pressure of the gas contained in the gas chamber 17 progressively increases.

Figure 3:
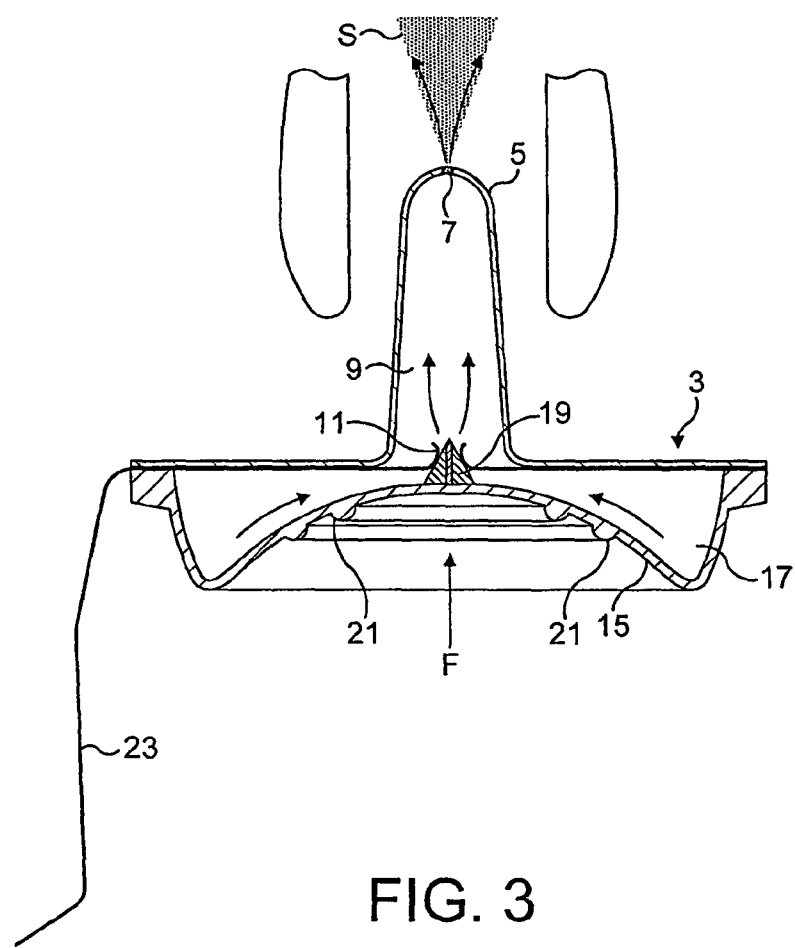
FIG. 3 illustrates a sectional view of the delivery device of FIG. 1 following actuation.

As illustrated in FIG. 3, at a predetermined point in the depression of the flexible member 15, the rupturing element 19 reaches the seal element 11 and acts to rupture the same. At this predetermined point, and through the depression of the flexible member 15, the gas in the gas chamber 17 has a predetermined pressure, and this pressurized gas passes into and through the substance chamber 9 such as to expel substance S from the delivery outlet 7 in the nosepiece 5.

In this embodiment the delivery device is fabricated using a "form, fill and seal" approach, where the body unit 3 is injection-moulded and utilizing a combination of vacuum-forming techniques with aluminium foil or metallized polymer materials.

Figure 4:
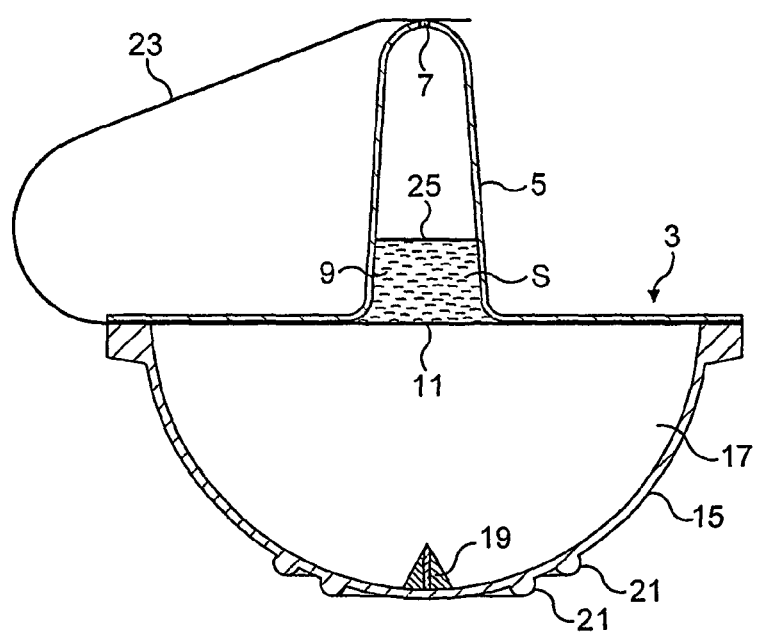
FIG. 4 illustrates a sectional view of a delivery device in accordance with a second embodiment of the present invention.
Figure 5:
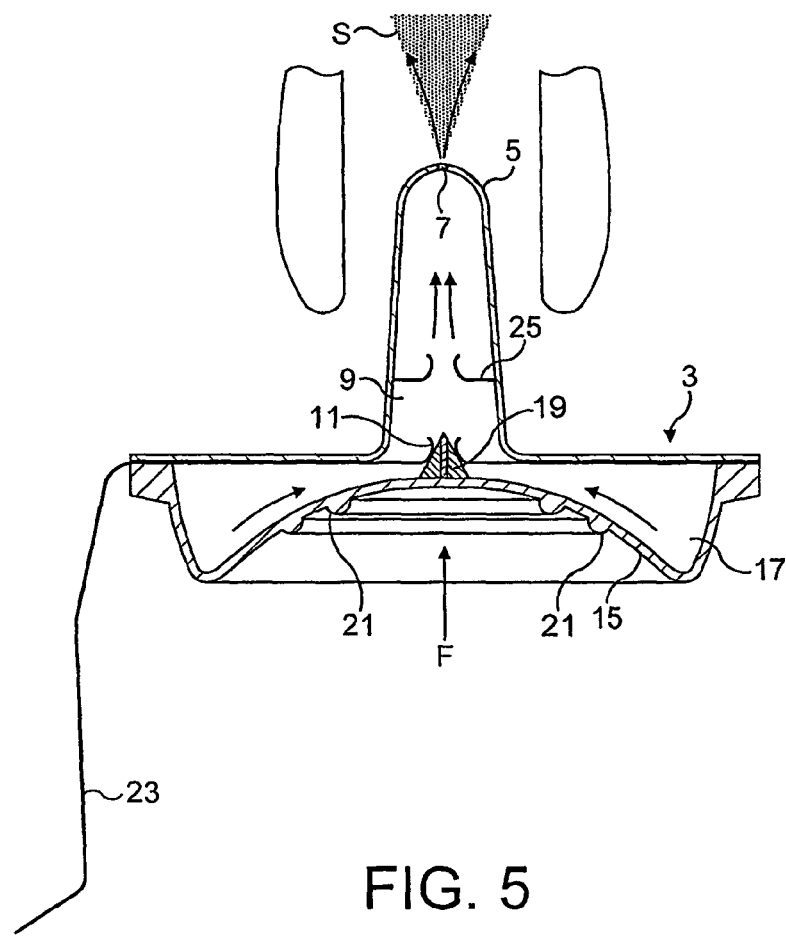
FIG. 5 illustrates a sectional view of the delivery device of FIG. 4 following actuation.

FIGS. 4 and 5 illustrate a delivery device in accordance with a second embodiment of the present invention.

The delivery device of this embodiment is quite similar to the delivery device of the above-described first embodiment, and thus, in order to avoid unnecessary duplication of description, only the differences will be described in detail.

The delivery device of this embodiment differs from that of the above-described first embodiment in that the substance chamber 9 is defined in part by first and second rupturable seal elements 11, 25, where the first seal element 11 has the same construction as the seal element 11 of the above-described first embodiment, and the second seal element 25 has a lower rupture strength than the predetermined gas pressure generated in the gas chamber 17 in actuation of the delivery device, such that the second seal element 25 is ruptured on being exposed to the generated gas pressure. With this configuration, the substance S to be delivered is contained within a closed environment, and the closure member 23 could be omitted.

Operation of the delivery device is identical to that of the above-described first embodiment, with the second seal element 25 being ruptured by the generated gas pressure subsequent to rupturing of the first seal element 11 by the rupturing element 19.

Figure 6:
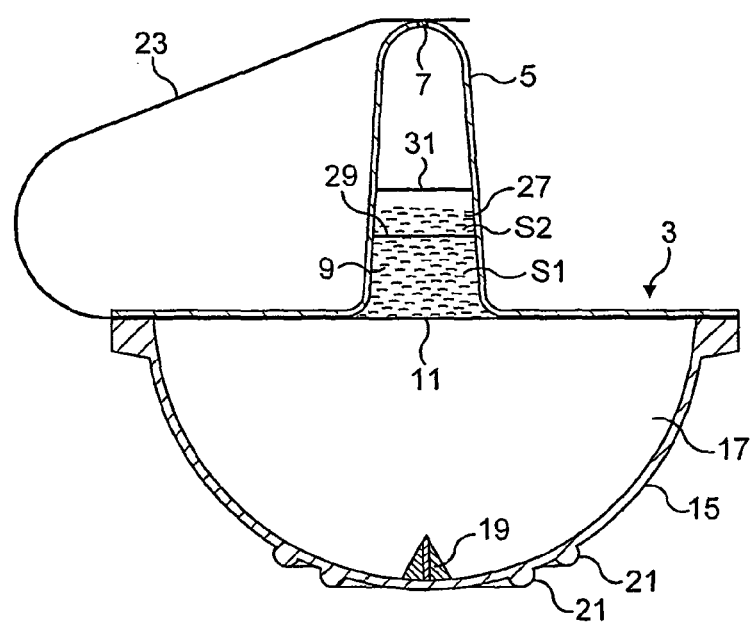
FIG. 6 illustrates a sectional view of a delivery device in accordance with a third embodiment of the present invention.
Figure 7:
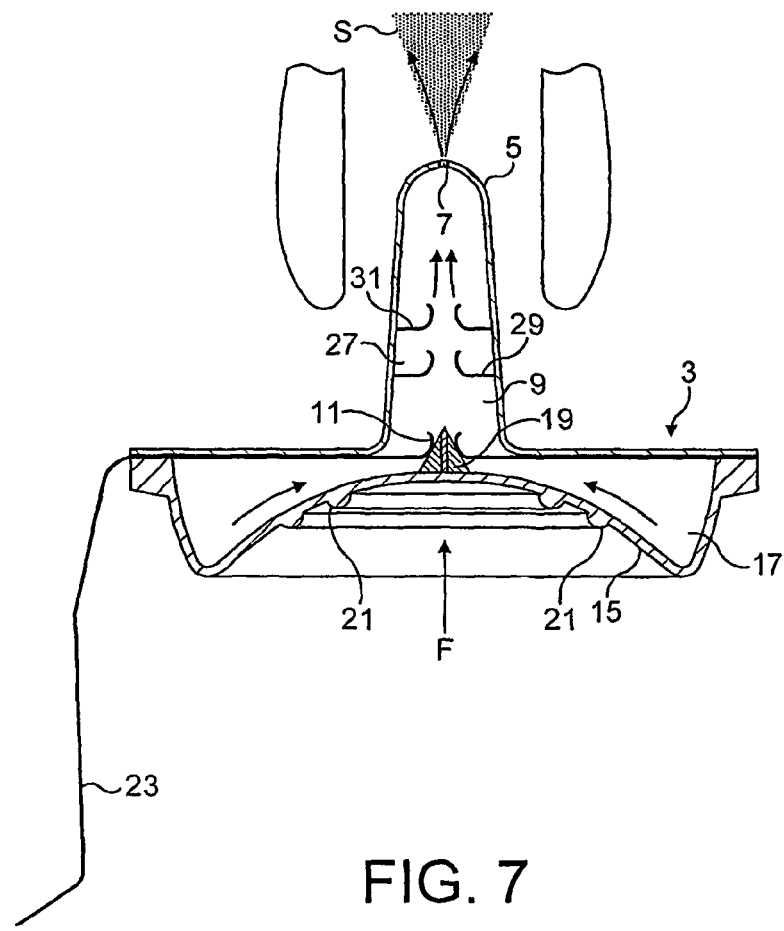
FIG. 7 illustrates a sectional view of the delivery device of FIG. 6 following actuation.

FIGS. 6 and 7 illustrate a delivery device in accordance with a third embodiment of the present invention.

The delivery device of this embodiment is quite similar to the delivery device of the above-described first embodiment, and thus, in order to avoid unnecessary duplication of description, only the differences will be described in detail.

The delivery device of this embodiment differs from that of the above-described first embodiment in comprising first and second substance chambers 9, 27 for separately containing first and second substances S1, S2 which are defined by respective ones of first to third rupturable seal elements 11, 29, 31, where the first seal element 11 has the same construction as the seal element 11 of the above-described first embodiment, and the second and third seal elements 29, 31 have lower rupture strengths than the predetermined gas pressure generated in the gas chamber 17 in actuation of the delivery device, such that the second and third seal elements 29, 31 are ruptured successively subsequent to being exposed to the generated gas pressure. This embodiment finds particular application in enabling the delivery of a required substance S which comprises first and second substances S1, S2 which would interact when stored together, and in enabling the constitution of a required substance S from first and second substances S1, S2, typically where the first substance S1 comprises a diluent and the second substance S2 comprises a powder which is to be re-constituted as a required liquid substance S by exposure to the diluent.

Operation of the delivery device is identical to that of the above-described first embodiment, with the second and third seal elements 29, 31 being ruptured by the generated gas pressure subsequent to rupturing of the first seal element 11 by the rupturing element 19.

Figure 8:
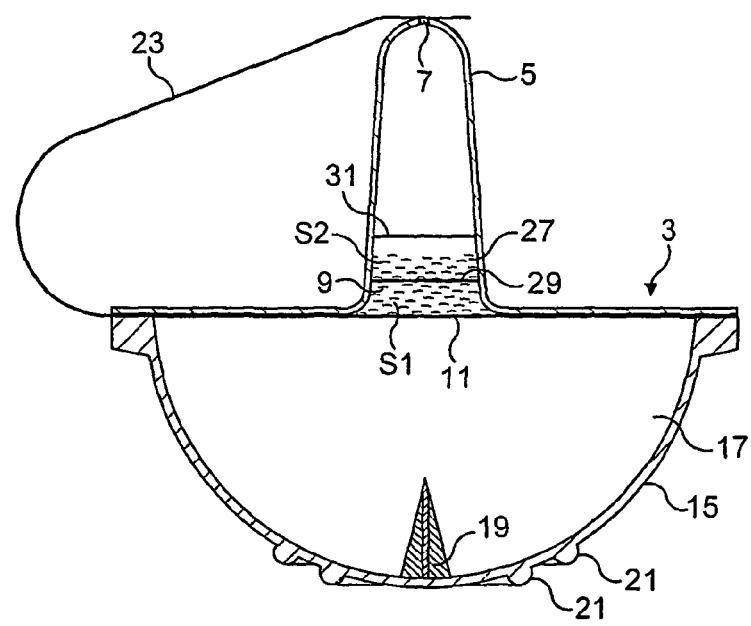
FIG. 8 illustrates a sectional view of a delivery device in accordance with a fourth embodiment of the present invention.
Figure 9:
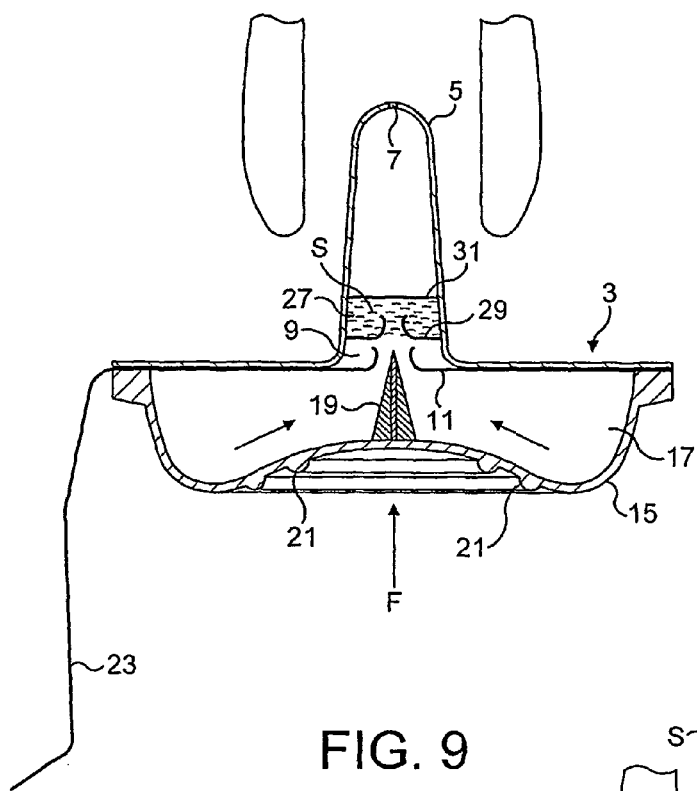
FIG. 9 illustrates a sectional view of the delivery device of FIG. 8 during actuation.
Figure 10:
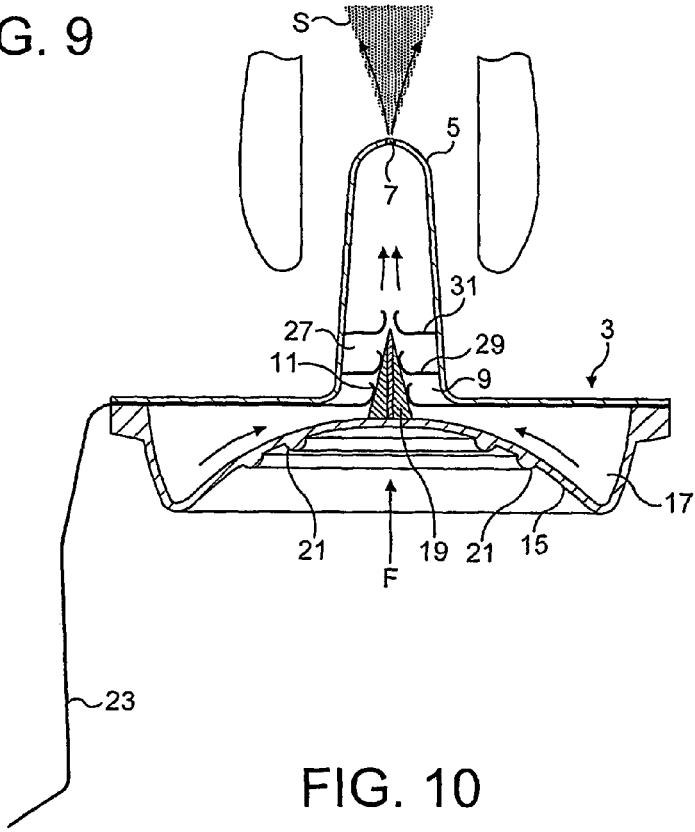
FIG. 10 illustrates a sectional view of the delivery device of FIG. 8 following actuation.

FIGS. 8 to 10 illustrate a delivery device in accordance with a fourth embodiment of the present invention.

The delivery device of this embodiment is quite similar to the delivery device of the above-described first embodiment, and thus, in order to avoid unnecessary duplication of description, only the differences will be described in detail.

The delivery device of this embodiment differs from that of the above-described first embodiment in comprising first and second substance chambers 9, 27 for separately containing first and second substances S1, S2 which are defined by respective ones of first to third rupturable seal elements 11, 29, 31, and in that the rupturing element 19 is extended such as to reach the third seal element 31 in actuation of the delivery device, where the first and third seal elements 11, 31 have the same construction as the seal element 11 of the above-described first embodiment, in being required to be ruptured by the rupturing element 19, and the second seal element 29 has a lower rupture strength than the predetermined gas pressure generated in the gas chamber 17 in actuation of the delivery device, such that the second seal element 29 is ruptured on being exposed to the generated gas pressure. This embodiment finds particular application in enabling the constitution of a required substance S from first and second substances S1, S2, typically where the first substance S1 comprises a diluent and the second substance S2 comprises a powder which is to be re-constituted as a required liquid substance S by exposure to the diluent.

Operation of the delivery device is identical to that of the above-described first embodiment, with the first seal element 11 first being ruptured by the rupturing element 19 on being advanced through depression of the flexible member 15, the second seal element 29 being ruptured by the generated gas pressure subsequent to rupturing of the first seal element 11 and thereby providing for the mixing of the first and second substances S1, S2 to re-constitute the required substance S, as illustrated in FIG. 9, and the third seal element 31 being ruptured by the rupturing element 19 on further advancement thereof through depression of the flexible member 15, at which point the gas within the gas chamber 17 is at the predetermined delivery pressure.

Figure 11:
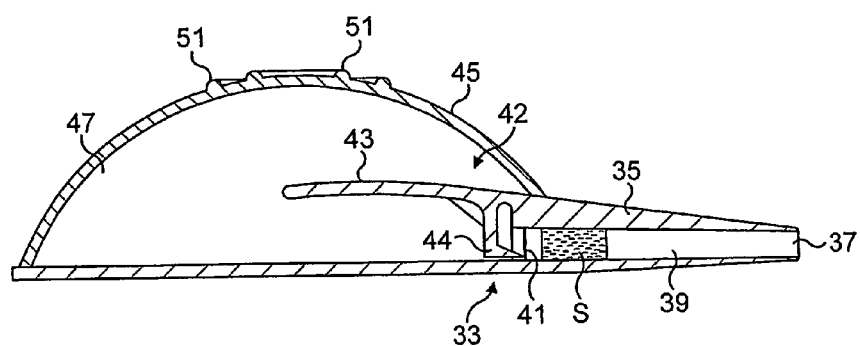
FIG. 11 illustrates a sectional view of a delivery device in accordance with a fifth embodiment of the present invention.
Figure 12:
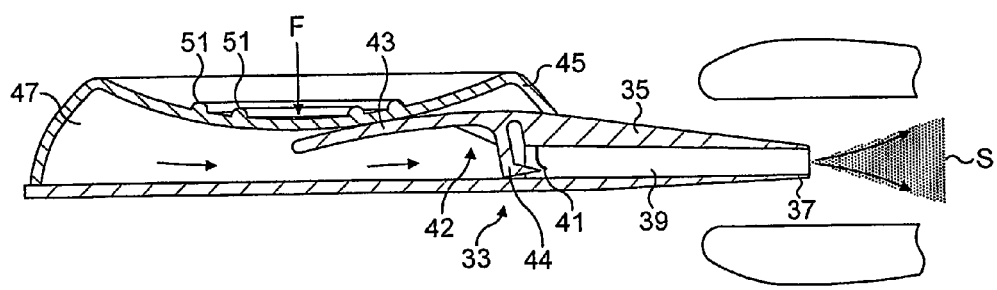
FIG. 12 illustrates a sectional view of the delivery device of FIG. 11 following actuation.

FIGS. 11 and 12 illustrate a delivery device in accordance with a fifth embodiment of the present invention.

In this embodiment the delivery device is configured as a unit-dose, disposable nasal delivery device for delivering substance to a nasal airway of a subject.

The delivery device comprises a body unit 33 which comprises a nosepiece 35 for insertion into a nostril of a subject which includes a delivery outlet 37 from which substance S is delivered, a substance chamber 39 in fluid communication with the delivery outlet 37 which is defined in part by a rupturable seal element 41, in this embodiment a frangible membrane, here a film, and contains substance S to be delivered, and a rupturing mechanism 42 which is actuatable to rupture the seal element 41, as will be described in more detail hereinbelow.

In this embodiment the substance S is a powder, but in another embodiment could equally be a liquid. For embodiments which deliver liquids, the delivery outlet 37 can be configured to deliver the liquid as an aerosol spray, that is, as liquid particles, or a liquid jet, that is, as a column of liquid.

In this embodiment the nosepiece 35 has an elongate tubular body, here of frusto-conical shape, which defines the substance chamber 39 and includes the delivery outlet 37 at one, forward end thereof and the seal element 41 at the other, rear end thereof.

In this embodiment the rupturing mechanism 42 comprises an actuating arm 43 and a rupturing element 44, here a sharp spike, which is supported by the actuating arm 43, with the actuating arm 43 being movable, here resiliently hinged to the rear end of the nosepiece 35, between a first, normal position, as illustrated in FIG. 11, in which the rupturing element 44 is disposed adjacent the seal element 41 and a second, actuated position, as illustrated in FIG. 12, in which the actuating arm 43 is deflected such as to cause the rupturing element 44 to rupture the seal element 41.

The delivery device further comprises a flexible member 45, in this embodiment an outwardly-projecting diaphragm, here dome-shaped, typically part-spherical, and in one embodiment hemi-spherical, which is disposed to the body unit 33 such as to enclose the rupturing mechanism 42 and define a compressible gas chamber 47 which is in fluid communication with a surface of the seal element 41 which is opposite the substance chamber 39. The flexible member 45 is configured such as to be depressed by a subject in applying an actuating force F to actuate the delivery device. In depressing the flexible member 45, typically through the application of a thumb of the subject where gripping the body unit 33 in ones of the forefingers, the pressure of the gas contained in the gas chamber 47 progressively increases to generate a gas supply which is at a predetermined pressure sufficient to expel the substance S from the substance chamber 39 and through the delivery outlet 37 in the nosepiece 35, and, on depression of the flexible member 45 to a predetermined extent, the rupturing mechanism 42 is actuated through movement of the actuating arm 43 thereof to the actuated position.

In this embodiment the seal element 41 has a rupture strength which exceeds the pressure which can be generated in the gas chamber 47, such that actuation of the delivery device requires the rupturing element 44 of the rupturing mechanism 42 to rupture the seal element 41, and, in requiring the flexible member 45 to be advanced to a predetermined extent to cause the rupturing element 44 to rupture the seal element 41, the generation of a predetermined pressure in the gas chamber 47 can be ensured prior to actuation of the delivery device.

In this embodiment, the flexible member 45 is configured, here including annular ribs 51, to provide for a controlled deformation of the flexible member 45 on being depressed, thereby ensuring the generation of a predetermined pressure in the gas chamber 47 at the point of the rupturing element 44 rupturing the seal element 41, and avoiding the possibility of the flexible member 45 being depressed in a non-uniform manner which could result in the rupturing element 44 rupturing the seal element 41 without the predetermined gas pressure having been achieved.

Operation of the delivery device will now be described hereinbelow.

A subject first inserts the nosepiece 35 into one of his/her nostrils.

The subject then depresses the flexible member 45, typically by the application of his/her thumb when gripping the body unit 33 in his/her forefingers. In depressing the flexible member 45, the pressure of the gas contained in the gas chamber 47 progressively increases.

As illustrated in FIG. 12, at a predetermined point in the depression of the flexible member 45, the actuating arm 43 of the rupturing mechanism 42 is moved such that the rupturing element 44 reaches the seal element 41 and acts to rupture the same. At this predetermined point, and through the depression of the flexible member 45, the gas in the gas chamber 47 has a predetermined pressure, and this pressurized gas passes into and through the substance chamber 39 such as to expel substance S from the delivery outlet 37 in the nosepiece 35.

In this embodiment the delivery device is fabricated using a "form, fill and seal" approach, where the body unit 33 is injection-moulded and utilizing a combination of vacuum-forming techniques with aluminium foil or metallized polymer materials.

Figure 13:
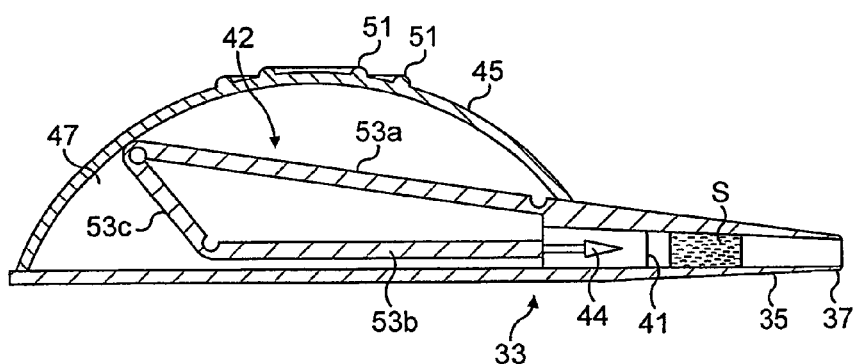
FIG. 13 illustrates a sectional view of a delivery device in accordance with a sixth embodiment of the present invention.
Figure 14:
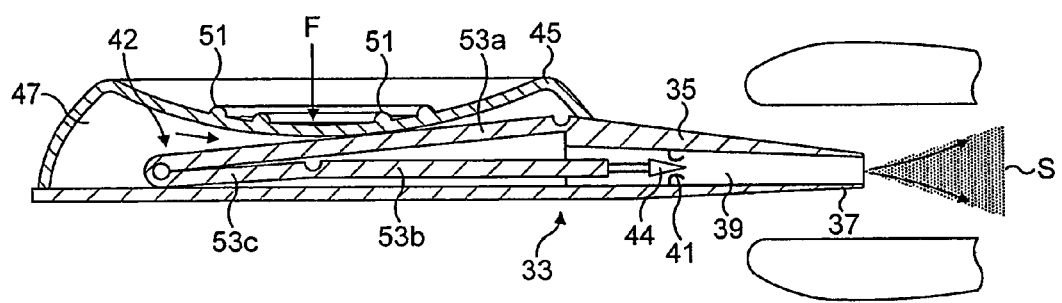
FIG. 14 illustrates a sectional view of the delivery device of FIG. 13 following actuation.

FIGS. 13 and 14 illustrate a delivery device in accordance with a sixth embodiment of the present invention.

The delivery device of this embodiment is quite similar to the delivery device of the above-described fifth embodiment, and thus, in order to avoid unnecessary duplication of description, only the differences will be described in detail.

The delivery device of this embodiment differs from that of the above-described fifth embodiment in that the rupturing mechanism 42 comprises a hinged link assembly 53, in this embodiment resiliently hinged as a single unit, which supports the rupturing element 44 such as to provide for movement of the same to the actuated position, in which the rupturing element 44 ruptures the seal element 41, on depression of the flexible member 45 to a predetermined point.

In this embodiment the rupturing mechanism 42 comprises a first link 53a which is hinged, here resiliently hinged, at one end thereof to the rear end of the nosepiece 35, a second link 53b which supports the rupturing element 44 at one, forward end thereof, and a third link 53c which couples the respective other ends of the first and second links 53a, 53b, where the other end of the first link 53a is located beyond the other end of the second link 53b in the sense of movement of the second link 53b. With this configuration, depression of the flexible member 45 acts to hinge the first link 53a relative to the nosepiece 35, and this movement of the first link 53a, through the coupling provided by the third link 53c, acts to drive the second link 53b forwardly to cause the rupturing element 44, as supported thereby, to rupture the seal element 41.

Operation of the delivery device is the same as for that of the above-described fifth embodiment.

Figure 15:
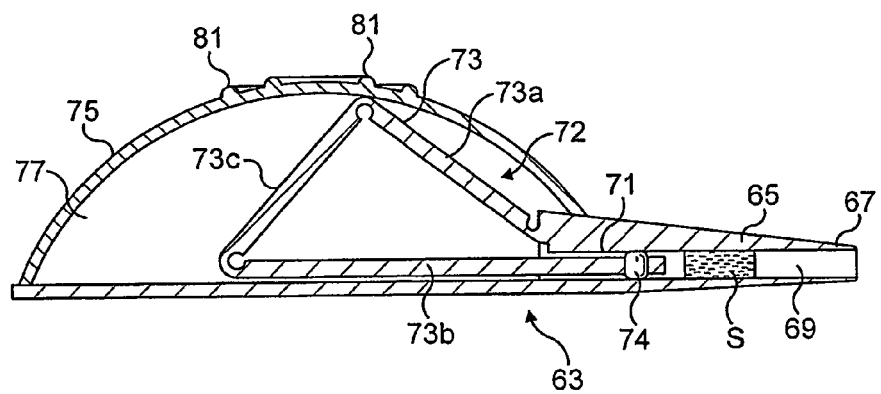
FIG. 15 illustrates a sectional view of a delivery device in accordance with a seventh embodiment of the present invention.
Figure 16:
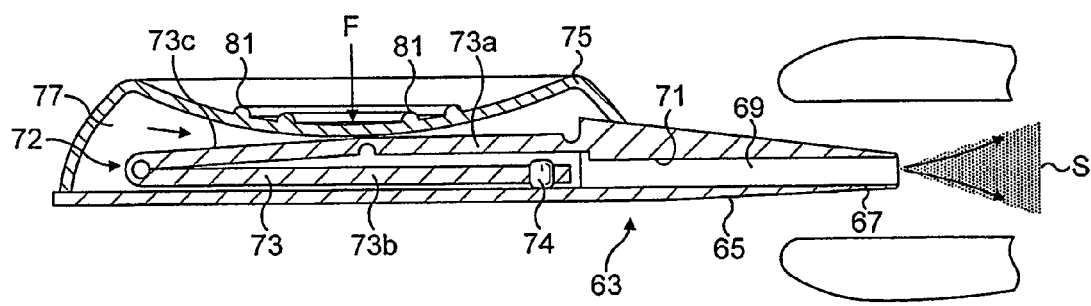
FIG. 16 illustrates a sectional view of the delivery device of FIG. 15 following actuation.

FIGS. 15 and 16 illustrate a delivery device in accordance with a seventh embodiment of the present invention.

In this embodiment the delivery device is configured as a unit-dose, disposable nasal delivery device for delivering substance to a nasal airway of a subject.

The delivery device comprises a body unit 63 which comprises a nosepiece 65 for insertion into a nostril of a subject which includes a delivery outlet 67 from which substance S is delivered, a substance chamber 69 in fluid communication with the delivery outlet 67 which contains substance S to be delivered, a gas supply passage 71 which is in fluid communication with and disposed upstream of the substance chamber 69, and a valve mechanism 72 which is actuatable to open the gas supply passage 71, as will be described in more detail hereinbelow.

In this embodiment the substance S is a powder, but in another embodiment could equally be a liquid. For embodiments which deliver liquids, the delivery outlet 67 can be configured to deliver the liquid as an aerosol spray, that is, as liquid particles, or a liquid jet, that is, as a column of liquid.

In this embodiment the nosepiece 65 has an elongate tubular body, here of frusto-conical shape, which defines the substance chamber 69 and includes the delivery outlet 67 at one, forward end thereof and the gas supply passage 71 at the other, rear end thereof.

In this embodiment the valve mechanism 72 comprises a hinged link assembly 73, here resiliently hinged as a single unit, and a seal element 74 which is supported by the link assembly 73, such as to provide for movement of the seal element 74 from a first, normal closed position, as illustrated in FIG. 15, in which the seal element 74 acts to close the gas supply passage 71 and a second, actuated open position, as illustrated in FIG. 16, in which the gas supply passage 71 is open.

In this embodiment the valve mechanism 72 comprises a first link 73a which is hinged, here resiliently hinged, at one end thereof to the rear end of the nosepiece 65, a second link 73b which supports the seal element 74 at one, forward end thereof, and a third link 73c which couples the respective other ends of the first and second links 73a, 73b, where the other end of the second link 73b is located beyond the other end of the first link 73a in the sense of movement of the second link 73b. With this configuration, actuation of the delivery device acts to cause the first link 73a to be hinged relative to the nosepiece 65, and this movement of the first link 73a, through the coupling provided by the third link 73c, acts to drive the second link 73b rearwardly to open the gas supply passage 71.

The delivery device further comprises a flexible member 75, in this embodiment an outwardly-projecting diaphragm, here dome-shaped, typically part-spherical, and in one embodiment hemispherical, which is disposed to the body unit 63 such as to enclose the valve mechanism 72 and define a compressible gas chamber 77 which is in operative fluid communication with the gas supply passage 71. The flexible member 75 is configured to be depressed by a subject in applying an actuating force F to actuate the delivery device. In depressing the flexible member 75, typically through the application of a thumb of the subject where gripping the body unit 63 in ones of the forefingers, the pressure of the gas contained in the gas chamber 77 progressively increases to generate a gas supply which is at a predetermined pressure sufficient to expel the substance S from the substance chamber 69 and through the delivery outlet 67 in the nosepiece 65, and, on depression of the flexible member 75 to a predetermined extent, the valve mechanism 72 is actuated through withdrawal of the seal element 74 from the gas supply passage 71.

In this embodiment actuation of the delivery device requires the seal element 74 of the valve mechanism 72 to be driven from the gas supply passage 71, and, in requiring the flexible member 75 to be depressed to a predetermined extent to cause the seal element 74 to be driven from the gas supply passage 71, the generation of a predetermined pressure in the gas chamber 77 is ensured prior to actuation of the delivery device.

In this embodiment the flexible member 75 is configured, here including annular ribs 81, to provide for a controlled deformation of the flexible member 75 on being depressed, thereby ensuring the generation of a predetermined pressure in the gas chamber 77 at the point of the seal element 74 of the valve mechanism 72 being driven from the gas supply passage 71, and avoiding the possibility of the flexible member 75 being depressed in a non-uniform manner which could result in the seal element 74 being driven from the gas supply passage 71 without the predetermined gas pressure having been achieved.

Operation of the delivery device will now be described hereinbelow.

A subject first inserts the nosepiece 65 into one of his/her nostrils.

The subject then depresses the flexible member 75, typically by the application of his/her thumb when gripping the body unit 63 in his/her forefingers. In depressing the flexible member 75, the pressure of the gas contained in the gas chamber 77 progressively increases.

As illustrated in FIG. 16, at a predetermined point in the depression of the flexible member 75, the first link 73a of the valve mechanism 72 is hinged to an extent as to cause the seal element 74 to be driven from the gas supply passage 71, in this embodiment through the coupling provided by the third link 73c which acts to drive the second link 73b rearwardly to withdraw the seal element 74 from the gas supply passage 71. At this predetermined point, and through the depression of the flexible member 75, the gas in the gas chamber 77 has a predetermined pressure, and this pressurized gas passes into and through the substance chamber 69 such as to expel substance S from the delivery outlet 67 in the nosepiece 65.

In this embodiment the delivery device is fabricated using a "form, fill and seal" approach, where the body unit 63 is injection-moulded and utilizing a combination of vacuum-forming techniques with aluminium foil or metallized polymer materials.

Figure 17:
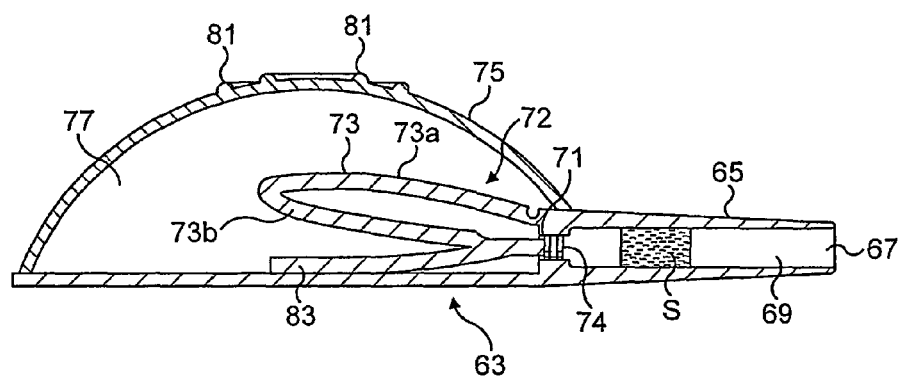
FIG. 17 illustrates a sectional view of a delivery device in accordance with an eighth embodiment of the present invention.
Figure 18:
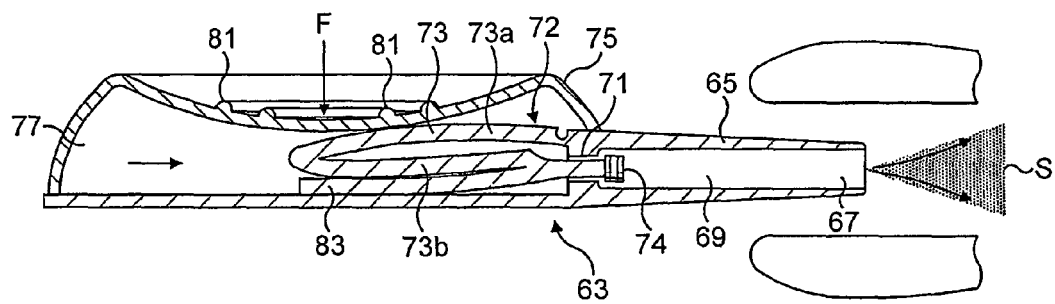
FIG. 18 illustrates a sectional view of the delivery device of FIG. 17 following actuation.

FIGS. 17 and 18 illustrate a delivery device in accordance with an eighth embodiment of the present invention.

The delivery device of this embodiment is quite similar to the delivery device of the above-described seventh embodiment, and thus, in order to avoid unnecessary duplication of description, only the differences will be described in detail.

The delivery device of this embodiment differs from that of the above-described seventh embodiment in that the gas supply passage 71 has a smaller radial dimension than the substance chamber 69, and in that the valve mechanism 72 is configured to drive the seal element 74 forwardly from sealing engagement with the gas supply passage 71 in actuation of the delivery device, in this embodiment by insertion into the substance chamber 69.

In this embodiment the valve mechanism 72 comprises only first and second links 73a, 73b, with the second link 73b being longer than the first link 73a, such that the second link 73b is driven forwardly on movement of the first link 73a through engagement with the flexible member 75. In this embodiment the second link 73b includes a supporting arm 83, here having a resilient structure, which acts to support the second link 73b in the closed position.

Operation of the delivery device is the same as for the delivery device of the above-described seventh embodiment, with the sealing element 74 being driven forwardly out of sealing engagement with the gas supply passage 71, as opposed to being driven rearwardly in being withdrawn from the gas supply passage 71.

Figure 19:
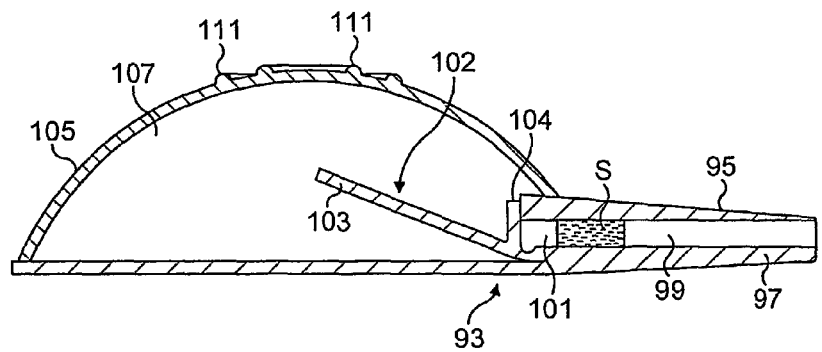
FIG. 19 illustrates a sectional view of a delivery device in accordance with a ninth embodiment of the present invention.
Figure 20:
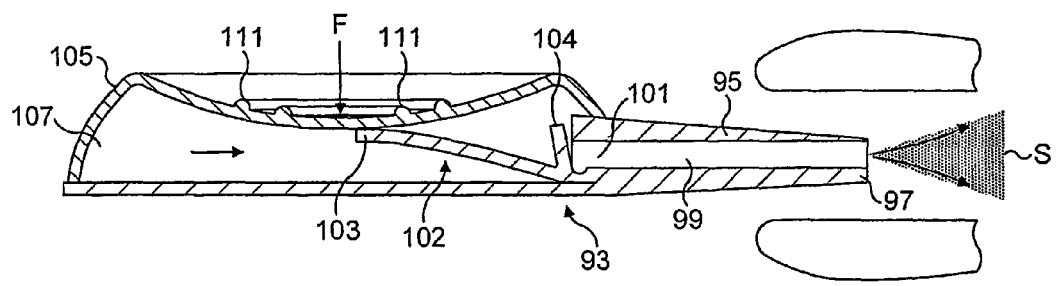
FIG. 20 illustrates a sectional view of the delivery device of FIG. 19 following actuation.

FIGS. 19 and 20 illustrate a delivery device in accordance with a ninth embodiment of the present invention.

In this embodiment the delivery device is configured as a unit-dose, disposable nasal delivery device for delivering substance to a nasal airway of a subject.

The delivery device comprises a body unit 93 which comprises a nosepiece 95 for insertion into a nostril of a subject which includes a delivery outlet 97 from which substance S is delivered, a substance chamber 99 in fluid communication with the delivery outlet 97 which contains substance S to be delivered, a gas supply passage 101 which is in fluid communication with and disposed upstream of the substance chamber 99, and a valve mechanism 102 which is actuatable to open the gas supply passage 101, as will be described in more detail hereinbelow.

In this embodiment the substance S is a powder, but in another embodiment could equally be a liquid. For embodiments which deliver liquids, the delivery outlet 97 can be configured to deliver the liquid as an aerosol spray, that is, as liquid particles, or a liquid jet, that is, as a column of liquid.

In this embodiment the nosepiece 95 has an elongate tubular body, here of frusto-conical shape, which defines the substance chamber 99 and includes the delivery outlet 97 at one, forward end thereof and the gas supply passage 101 at the other, rear end thereof.

In this embodiment the valve mechanism 102 comprises an actuating arm 103 and a seal element 104, here a flap, which is supported by the actuating arm 103, with the actuating arm 103 being movable, here hinged to the rear end of the nosepiece 95, between a first, normal closed position, as illustrated in FIG. 19, in which the seal element 104 closes the gas supply passage 101 and a second, actuated position, as illustrated in FIG. 20, in which the actuating arm 103 is deflected such as to release the seal element 104 from sealing engagement with the gas supply passage 101 and thereby open the same. In this embodiment the seal element 104 is normally biased into sealing engagement with the gas supply passage 101. In an alternative embodiment the seal element 104 could be bonded, typically adhered, in sealing engagement with the gas supply passage 101, with the bond being broken with a predetermined deflection of the actuating arm 103.

The delivery device further comprises a flexible member 105, in this embodiment an outwardly-projecting diaphragm, here dome-shaped, typically part-spherical, and in one embodiment hemi-spherical, which is disposed to the body unit 93 such as to enclose the valve mechanism 102 and define a compressible gas chamber 107 which is in operative fluid communication with the gas supply passage 101. The flexible member 105 is configured to be depressed by a subject in applying an actuating force F to actuate the delivery device.

In depressing the flexible member 105, typically through the application of a thumb of the subject where gripping the body unit 93 in ones of the forefingers, the pressure of the gas contained in the gas chamber 107 progressively increases to generate a gas supply which at a predetermined pressure sufficient to expel the substance S from the substance chamber 99 and through the delivery outlet 97 in the nosepiece 95, and, on compression of the flexible member 105 to a predetermined extent, the valve mechanism 102 is actuated through movement of the actuating arm 103 to the actuated position.

In this embodiment actuation of the delivery device requires the seal element 104 of the valve mechanism 102 to be released from sealing engagement with the gas supply passage 101, and, in requiring the flexible member 105 to be depressed to a predetermined extent to cause the seal element 104 of the valve mechanism 102 to be released from sealing engagement with the gas supply passage 101, the generation of a predetermined pressure in the gas chamber 107 is ensured prior to actuation of the delivery device.

In this embodiment, the flexible member 105 is configured, here including annular ribs 111, to provide for a controlled deformation of the flexible member 105 on being depressed, thereby ensuring the generation of a predetermined pressure in the gas chamber 107 at the point of the seal element 104 of the valve mechanism 102 being released from sealing engagement with the gas supply passage 101, and avoiding the possibility of the flexible member 105 being depressed in a non-uniform manner which could result in the seal element 104 being released from sealing engagement with the gas supply passage 101 without the predetermined gas pressure having been achieved.

Operation of the delivery device will now be described hereinbelow.

A subject first inserts the nosepiece 95 into one of his/her nostrils.

The subject then depresses the flexible member 105, typically by the application of his/her thumb when gripping the body unit 93 in his/her forefingers. In depressing the flexible member 105, the pressure of the gas contained in the gas chamber 107 progressively increases.

As illustrated in FIG. 20, at a predetermined point in the depression of the flexible member 105, the actuating arm 103 of the valve mechanism 102 is moved to an extent as to cause release of the seal element 104 from sealing engagement with the gas supply passage 101. At this predetermined point, and through the depression of the flexible member 105, the gas in the gas chamber 107 has a predetermined pressure, and this pressurized gas passes into and through the substance chamber 99 such as to expel substance S from the delivery outlet 97 in the nosepiece 95.

In this embodiment the delivery device is fabricated using a "form, fill and seal" approach, where the body unit 93 is injection-moulded and utilizing a combination of vacuum-forming techniques with aluminium foil or metallized polymer materials.

Figure 21:
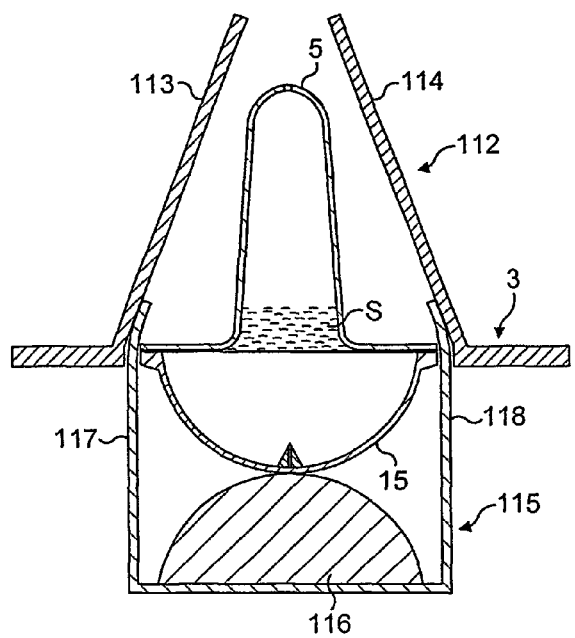
FIG. 21 illustrates a sectional view of a delivery device as one modification of the delivery device of FIG. 1.
Figure 22:
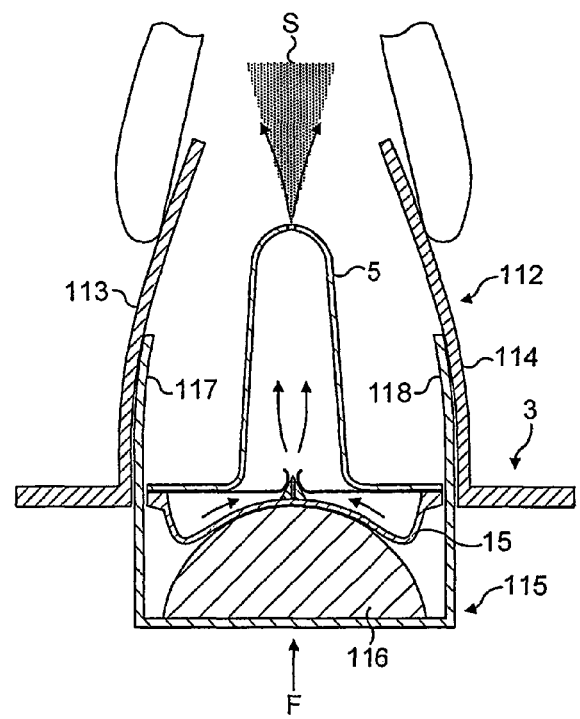
FIG. 22 illustrates a sectional view of the delivery device of FIG. 21 following actuation.

FIGS. 21 and 22 illustrate a nasal delivery device as one modification of the delivery device of the above-described first embodiment of the present invention.

The delivery device further comprises an expansion mechanism 112 which acts to expand the nasal cavity of the subject into which the nosepiece 5 is inserted on actuation of the delivery device. In one embodiment the expansion mechanism 112 can provide for sealing with the nasal cavity of the subject.

In this embodiment the expansion mechanism 112 comprises first and second expansion arms 113, 114, here flexible elements, which extend forwardly from the body unit 3 and laterally on opposed sides of the nosepiece 5, and an actuation member 115 to which an actuation force F is applied by the subject in actuating the delivery device such as to be depressed and thereby effect expansion of the expandable arms 113, 114. In an alternative embodiment the expansion arms 113, 114 could be pivotally hinged to the body unit 3, as opposed to being resiliently hinged in this embodiment.

In this embodiment the actuation member 115 comprises a body 116 which engages the flexible member 15, and first and second biasing arms 117, 118 which extend forwardly of the body 116 adjacent respective ones of the first and second expansion arms 113, 114 such as to slide thereagainst on depression of the actuation member 115 and cause expansion of the expansion arms 113, 114, thereby expanding the nasal cavity, and in particular the anterior nasal valve. In this embodiment the biasing arms 117, 118 comprise resilient elements which act to bias the respective expansion arms 113, 114 outwardly.

It will be appreciated that the above-described second to fourth embodiments could be similarly modified.

Figure 23:
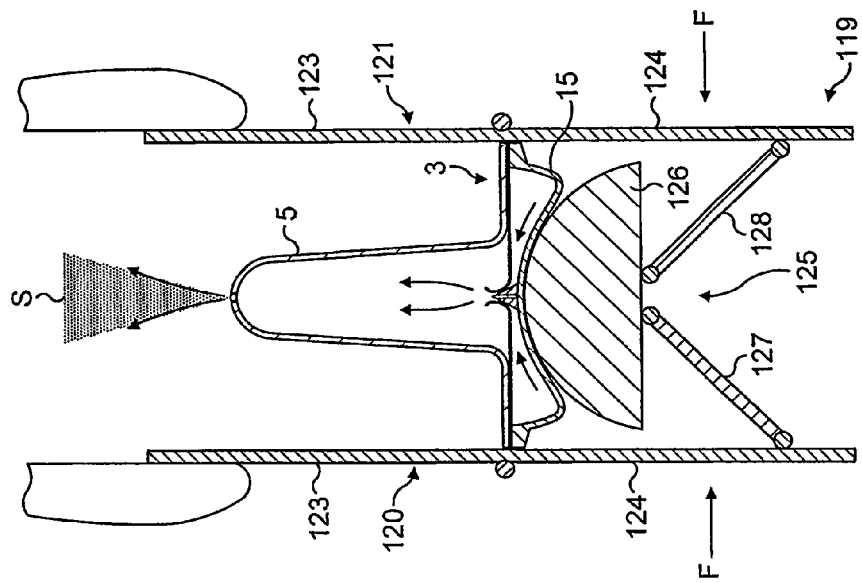
FIG. 23 illustrates a sectional view of a delivery device as another modification of the delivery device of FIG. 1.
Figure 24:
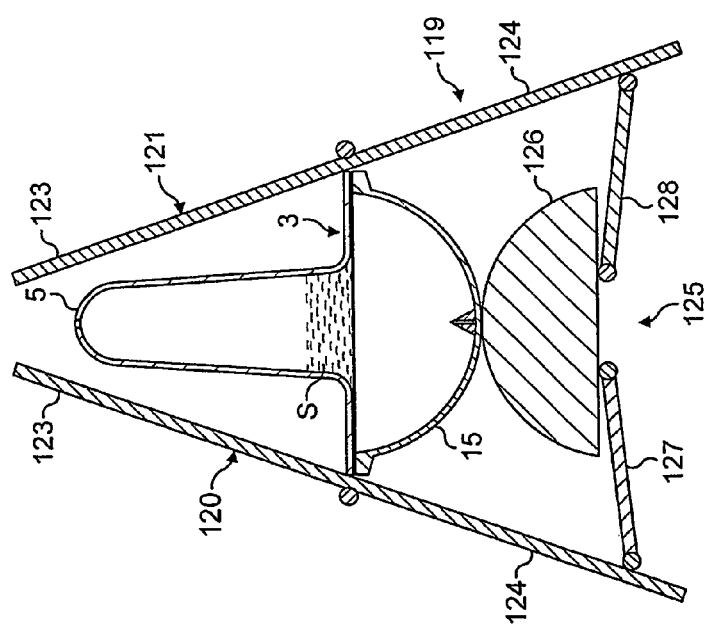
FIG. 24 illustrates a sectional view of the delivery device of FIG. 23 following actuation.

FIGS. 23 and 24 illustrate a nasal delivery device as another modification of the delivery device of the above-described first embodiment of the present invention.

The delivery device further comprises an expansion mechanism 119 which acts to expand the nasal cavity of the subject into which the nosepiece 5 is inserted on actuation of the delivery device. In one embodiment the expansion mechanism 119 can provide for sealing with the nasal cavity of the subject.

The expansion mechanism 119 comprises first and second levers 120, 121 which are hinged, here pivotally hinged, to opposed sides of the body unit 3. The first and second levers 120, 121 each comprise a first expansion arm 123 which extends forwardly from the body unit 3 and laterally of the nosepiece 5 and a second biasing arm 124 which extends rearwardly of the body unit 3, whereby, when the subject applies an actuation force F to each of the respective biasing arms 124, typically by gripping between a thumb and ones of the forefingers of the subject, the expansion arms 123 expand, thereby expanding the nasal cavity, and in particular the anterior nasal valve.

The expansion mechanism 119 further comprises an actuation member 125 which comprises a body 126 which engages the flexible member 15, and first and second links 127, 128 which couple the respective ones of the biasing arms 124, 124 to the body 126 such as to provide for the body 126 to be advanced, thereby depressing the flexible member 15, on closing the biasing arms 124 in applying an actuation force F thereto.

It will be appreciated that the above-described second to fourth embodiments could be similarly modified.

Figure 25:
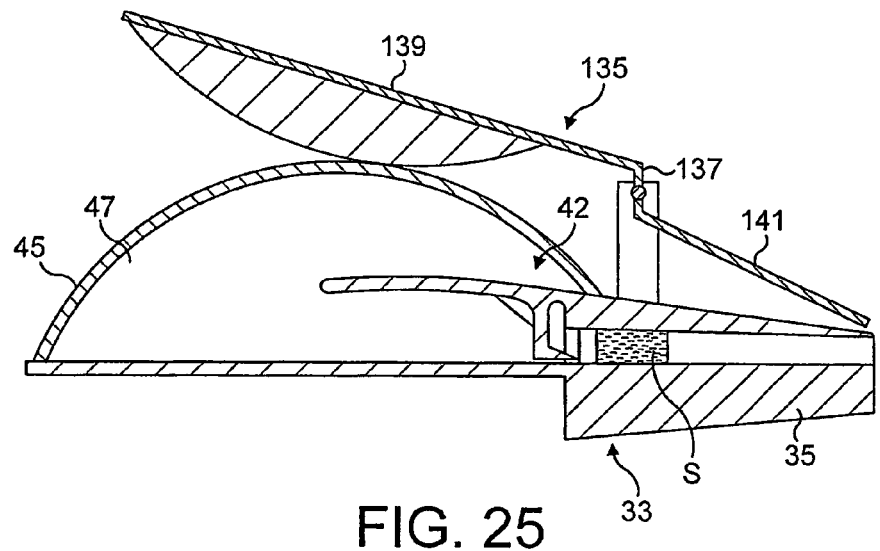
FIG. 25 illustrates a sectional view of a delivery device as another modification of the delivery device of FIG. 10.
Figure 26:
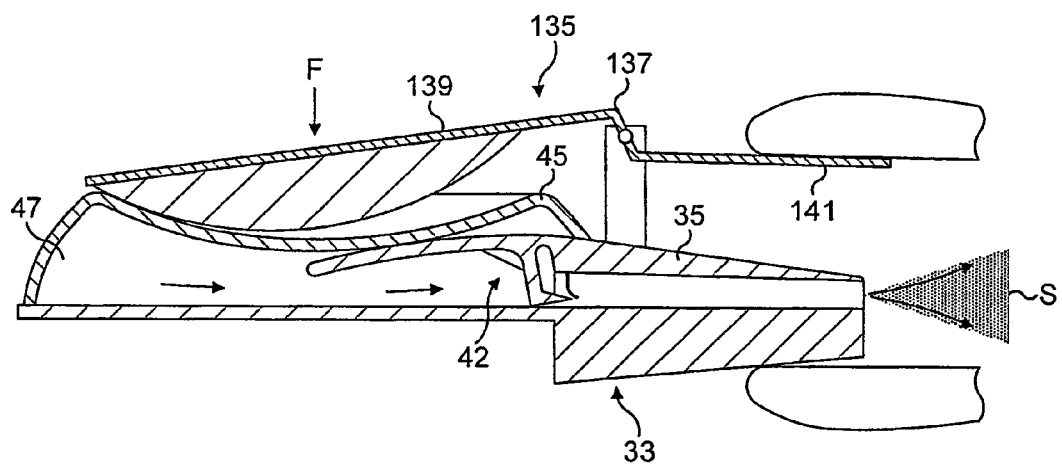
FIG. 26 illustrates a sectional view of the delivery device of FIG. 25 following actuation.

FIGS. 25 and 26 illustrate a nasal delivery device as a modification of the delivery device of the above-described fifth embodiment of the present invention.

The delivery device further comprises an expansion mechanism 135 which acts to expand the nasal cavity of the subject into which the nosepiece 35 is inserted on actuation of the delivery device. In one embodiment the expansion mechanism 135 can provide for sealing with the nasal cavity of the subject.

In this embodiment the expansion mechanism 135 comprises a lever 137 which is hinged to the body unit 33, and comprises a first loading arm 139 which extends over the flexible member 45 and is acted upon to depress the flexible member 45, and a second expansion arm 141 which extends adjacent one side of the nosepiece 35 and is moved outwardly on depression of the loading arm 139, thereby expanding the nasal cavity, and in particular the anterior nasal valve.

It will be appreciated that the above-described sixth to ninth embodiments could be similarly modified.

Finally, it will be understood that the present invention has been described in its preferred embodiments and can be modified in many different ways without departing from the scope of the invention as defined by the appended claims.

In the various implementations of this invention, opening mechanism geometries, barrier seal burst pressures, and different nozzle types and geometries may be utilized to produce delivery devices with a range of applications.

The present invention could also be implemented as a multi-dose device where including one or more sacrificial elements that are replaced for each operation in conjunction with other components that are reused.

Also, for oral and nasal delivery devices, the delivery devices can incorporate a mouthpiece through which a subject exhales to provide for closure of the oropharyngeal velum during actuation of the delivery devices. In one embodiment the delivery devices can be breath-actuated.

Further, in other embodiments, as nasal delivery devices and by providing for a fluid-tight seal with the nosepiece 5, 35, 65, 95, the delivery devices can be configured to deliver substance through one nostril of a subject at such a pressure as to flow around the posterior margin of the nasal septum and out of the other nostril of the subject, thereby achieving bi-directional delivery through the nasal cavities as disclosed in WO-A-00/51672, the content of which is herein incorporated by reference. In addition, a supplementary gas flow, in one embodiment derived from the exhalation breath of a subject, can be provided to provide for such bi-directional delivery.

In addition, the present invention finds application other than as a nasal delivery device, such as an oral delivery device or a topical delivery device, and, indeed, in a range of non-healthcare applications where controlled delivery of substance, as either a powder or liquid, is required.

The invention claimed is:

1. A device actuatable to deliver substance into a cavity, comprising:
    a delivery outlet from which substance is in use delivered;
    a gas chamber containing a gas and being of reducible volume, wherein a reduction in the volume of the gas chamber to a predetermined volume acts to pressurize the contained gas to a predetermined pressure;
    a seal element disposed between the gas chamber and the delivery outlet; and
    an opening mechanism configured, on reduction of the volume of the gas chamber to a predetermined volume, to open the seal element, whereupon a gas flow from the gas chamber acts to deliver substance from the delivery outlet; and
    an expansion mechanism configured to expand a cavity into which the device, in use, is inserted,
wherein the device is configured such that application of an actuation force to the device causes an expansion of the expansion mechanism to expand the cavity and the device to deliver substance into the cavity.

2. The delivery device of claim 1, wherein the gas chamber is defined in part by a flexible member to which an actuating force is in use applied in actuating the delivery device, with the actuating force acting to depress the flexible member such as to reduce the volume of the gas chamber and pressurize the gas contained therein.

3. The delivery device of claim 2, wherein the flexible member comprises an outwardly-projecting member which is depressed on application of an actuating force.

4. The delivery device of claim 3, wherein the flexible member comprises a dome-shaped member.

5. The delivery device of claim 3, wherein the flexible member is configured such as to provide for deflection thereof in a controlled, predetermined fashion in depressing the same on application of an actuating force.

6. The delivery device of claim 5, wherein the flexible member is one or both of shaped or sized to provide for controlled deflection.

7. The delivery device of claim 6, wherein the flexible member includes ribs which provide for controlled deflection.

8. The delivery device of claim 2, wherein the seal element comprises a rupturable element, and the opening mechanism includes a rupturing element which acts to rupture the rupturable element on depression of the flexible member to a predetermined extent.

9. The delivery device of claim 8, wherein the rupturing element is supported at an inner surface of the flexible member in opposed relation to the rupturable element such as to be moved in a direction of an actuating force as applied to the flexible member.

10. The delivery device of claim 8, wherein the opening mechanism comprises an actuating arm which supports the rupturing element, with the actuating arm being movably disposed relative to the rupturable element on engagement by the flexible member, such that, on depression of the flexible member to a predetermined extent, the actuating arm is moved such as to cause the rupturing element to rupture the rupturable element.

11. The delivery device of claim 10, wherein the actuating arm is hingeably supported such that the rupturing element is rotated to rupture the rupturable element.

12. The delivery device of claim 8, wherein the opening mechanism comprises a link assembly which supports the rupturing element, with the link assembly being movable relative to the rupturable element on engagement by the flexible member, such that, on depression of the flexible member to a predetermined extent, the link assembly is moved such as to cause the rupturing element to rupture the rupturable element.

13. The delivery device of claim 12, wherein the link assembly comprises first, second and third hinged links, with the first link being hinged relative to the rupturable element, the second link supporting the rupturing element at one, forward end thereof and the third link coupling the respective other ends of the first and second links, whereby depression of the flexible member acts to hinge the first link relative to the rupturable element, which movement, through the coupling provided by the third link, acts to drive the second link forwardly to cause the rupturing element supported thereby to rupture the rupturable element.

14. The delivery device of claim 2, wherein the seal element comprises a valve element, and the opening mechanism is configured to release the valve element on depression of the flexible member to a predetermined extent.

15. The delivery device of claim 14, further comprising:
    a gas supply passage operatively in fluid communication with the delivery outlet; and
    wherein the valve element is normally in a closed position in sealing engagement with the gas supply passage, and moved to an open position out of sealing engagement with the gas supply passage by the opening mechanism on depression of the flexible member to a predetermined extent.

16. The delivery device of claim 15, wherein the opening mechanism comprises a link assembly which supports the valve element, with the link assembly being movable relative to the gas supply passage on engagement by the flexible member, such that, on depression of the flexible member to a predetermined extent, the link assembly is moved such as to cause the valve element to be moved to the open position.

17. The delivery device of claim 16, wherein the link assembly comprises first, second and third hinged links, with the first link being hinged relative to the gas supply passage, the second link supporting the valve element at one, forward end thereof and the third link coupling the respective other ends of the first and second links, whereby depression of the flexible member acts to hinge the first link relative to the gas supply passage, which movement, through the coupling provided by the third link, acts to drive the second link to cause the valve element supported thereby to be moved to the open position.

18. The delivery device of claim 17, wherein the link assembly is configured such that the valve element is withdrawn from the gas supply passage on depression of the flexible member to a predetermined extent.

19. The delivery device of claim 16, wherein the link assembly comprises first and second hinged links, with the first link being hinged relative to the gas supply passage and the second link supporting the valve element at one, forward end thereof, whereby depression of the flexible member acts to hinge the first link relative to the gas supply passage, which movement acts to drive the second link to cause the valve element supported thereby to be moved to the open position.

20. The delivery device of claim 19, wherein the valve element is pushed from the gas supply passage on depression of the flexible member to a predetermined extent.

21. The delivery device of claim 19, wherein the link assembly further comprises a supporting arm which acts normally to support the link assembly such that the valve element is in the closed position.

22. The delivery device of claim 15, wherein the opening mechanism comprises an actuating arm which supports the valve element, with the actuating arm being movably disposed relative to the gas supply passage on engagement by the flexible member, such that, on depression of the flexible member to a predetermined extent, the actuating arm is moved such as to move the valve element to the open position.

23. The delivery device of claim 22, wherein the actuating arm is hingeably supported such that the valve element is rotated from the closed position.

24. The delivery device of claim 23, wherein the valve element comprises a flap.

25. The delivery device of claim 22, wherein the valve element is normally biased to the gas supply passage in the closed position.

26. The delivery device of claim 22, wherein the valve element is bonded to the gas supply passage in the closed position.

27. The delivery device of claim 1, further comprising:
at least one substance chamber for containing substance operatively in fluid communication with the delivery outlet.

28. The delivery device of claim 27, comprising:
first and second substance chambers, each separately containing substance components which are combined for delivery.

29. The delivery device of claim 1, wherein the expansion mechanism provides for sealing engagement with the cavity.

30. The delivery device of claim 1, wherein the expansion mechanism comprises first and second expansion arms disposed in opposed relationship to respective sides of the delivery outlet, and an actuation member which in use is actuated by a subject in actuating the delivery device and effects expansion of the expansion arms.

31. The delivery device of claim 30, wherein the actuation member comprises an actuation body and first and second biasing arms extending forwardly of the actuation body such as to engage respective ones of the first and second expansion arms, whereby actuation of the actuation body acts to cause expansion of the first and second expansion arms.

32. The delivery device of claim 31, wherein the first and second biasing arms comprise resilient elements which act to bias respective ones of the first and second biasing arms outwardly.

33. The delivery device of claim 1, wherein the expansion mechanism comprises first and second levers which are pivotally hinged relative to opposed sides of the delivery outlet, each of the levers comprising a first, expansion arm extending forwardly and laterally of the delivery outlet and a second, biasing arm extending rearwardly, whereby, on application of an actuation force to the biasing arms such as to bias the same inwardly, the expansion arms are driven outwardly to effect expansion of the same.

34. The delivery device of claim 33, wherein the actuation member comprises an actuation body and first and second links which couple respective ones of the biasing arms to the actuation body.

35. The delivery device of claim 1, wherein the expansion mechanism comprises a lever which is hinged relative to delivery outlet, the lever comprising a loading arm which is acted upon by a subject in actuating the delivery device, and an expansion arm extending forwardly to one side of the delivery outlet, whereby the expansion arm is moved outwardly relative to the delivery outlet on a subject acting upon the loading arm.

36. The delivery device of claim 1, wherein the cavity is a nasal cavity.

37. The delivery device of claim 1, wherein the cavity is an oral cavity.

38. The delivery device of claim 1, wherein substance is delivered as a liquid.

39. The delivery device of claim 1, wherein substance is delivered as a powder.

40. A delivery device, comprising:
a gas-filled chamber of variable volume;
a delivery outlet coupled to the chamber and from which substance is deliverable, carried by the gas from the chamber;
a seal between the chamber and the delivery outlet;
opening means for opening the seal on reduction of the volume of the chamber to a predetermined volume, to allow the gas pressurized by the reduction in the volume of the chamber to flow through the delivery outlet; and
an expansion mechanism configured to expand a cavity into which the device, in use, is inserted,
wherein the device is configured such that application of an actuation force to the device causes an expansion of the expansion mechanism to expand the cavity and the device to deliver substance into the cavity.

41. The device of claim 1 or 40, wherein the cavity is a mammalian body cavity.

* * * * *

UNITED STATES PATENT AND TRADEMARK OFFICE
CERTIFICATE OF CORRECTION

| | | |
|---|---|---|
| PATENT NO. | : 7,934,503 B2 | Page 1 of 1 |
| APPLICATION NO. | : 10/520957 | |
| DATED | : May 3, 2011 | |
| INVENTOR(S) | : Per Gisle Djupesland et al. | |

It is certified that error appears in the above-identified patent and that said Letters Patent is hereby corrected as shown below:

In claim 1, at column 17, line 20, delete "and"

Signed and Sealed this
Fourth Day of October, 2011

David J. Kappos
*Director of the United States Patent and Trademark Office*